United States Patent
Weber et al.

(10) Patent No.: US 9,814,875 B2
(45) Date of Patent: *Nov. 14, 2017

(54) MEDICAL DEVICE WITH A STRUCTURED COATING

(71) Applicant: Cardiac Pacemakers, Inc., St. Paul, MN (US)

(72) Inventors: Jan Weber, Maastricht (NL); Torsten Scheuermann, Munich (DE); Stephen B. Ruble, Lino Lakes, MN (US); Barry L. Rudman, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 33 days.

This patent is subject to a terminal disclaimer.

(21) Appl. No.: 14/850,932

(22) Filed: Sep. 10, 2015

(65) Prior Publication Data

US 2016/0001062 A1    Jan. 7, 2016

Related U.S. Application Data

(63) Continuation-in-part of application No. 14/197,559, filed on Mar. 5, 2014, now Pat. No. 9,186,498.
(Continued)

(51) Int. Cl.
*A61N 1/05* (2006.01)
*A61L 29/08* (2006.01)
(Continued)

(52) U.S. Cl.
CPC ............ *A61N 1/056* (2013.01); *A61L 29/085* (2013.01); *A61L 29/14* (2013.01); *A61L 31/10* (2013.01);
(Continued)

(58) Field of Classification Search
CPC ...... A61L 31/14; A61L 2400/18; A61L 31/10; A61N 1/056
(Continued)

(56) References Cited

U.S. PATENT DOCUMENTS 5,312,427 A    5/1994  Shturman
8,114,153 B2   2/2012  Holman et al.
(Continued)

FOREIGN PATENT DOCUMENTS

CN    101808677 A    8/2010
JP    2005050719 A    2/2005
(Continued)

OTHER PUBLICATIONS

Arifuzzaman, Shafi et al., Formation of surface-grafted polymeric amphiphilic coatings comprising ethylene glycol and fluorinated groups and their response to protein adsorption, Biointerphases, vol. 4, No. 2, Jun. 2009, pp. FA33-44.
(Continued)

*Primary Examiner* — Alyssa M Alter
(74) *Attorney, Agent, or Firm* — Faegre Baker Daniels LLP

(57) ABSTRACT

A medical device includes a tubular body having a distal end and a proximal end, a lumen extending through the tubular body from the distal end to the proximal end, a wire extending through the lumen from the distal end to the proximal end, and a polymeric coating. The wire has an outer surface. The polymeric coating is on at least a portion of the outer surface of the wire. The coating comprises a bulk material and a plurality of flexible microstructures disposed on the bulk material. The microstructures extend outwardly from a surface of the polymeric coating.

20 Claims, 8 Drawing Sheets

Related U.S. Application Data

(60) Provisional application No. 61/773,471, filed on Mar. 6, 2013.

(51) Int. Cl.
    *A61L 29/14*     (2006.01)
    *A61L 31/10*     (2006.01)
    *A61L 31/14*     (2006.01)
    *A61B 17/3207*     (2006.01)
    *A61B 17/00*     (2006.01)
    *A61B 17/22*     (2006.01)

(52) U.S. Cl.
    CPC ............... *A61L 31/14* (2013.01); *A61N 1/05* (2013.01); *A61B 17/320758* (2013.01); *A61B 2017/0084* (2013.01); *A61B 2017/00845* (2013.01); *A61B 2017/00862* (2013.01); *A61B 2017/22094* (2013.01); *A61L 2400/18* (2013.01)

(58) Field of Classification Search
    USPC .......................................................... 607/116
    See application file for complete search history.

(56) References Cited

U.S. PATENT DOCUMENTS

| | | | |
|---|---|---|---|
| 9,186,498 B2* | 11/2015 | Weber | ............ A61L 31/10 |
| 2003/0139689 A1 | 7/2003 | Shturman et al. | |
| 2009/0054949 A1 | 2/2009 | Alexander et al. | |
| 2009/0171425 A1* | 7/2009 | Dahlberg | ............ A61N 1/05 |
| | | | 607/127 |
| 2010/0075018 A1 | 3/2010 | Desai et al. | |
| 2012/0172905 A1 | 7/2012 | Lee Shee et al. | |
| 2012/0239138 A1 | 9/2012 | Weber et al. | |
| 2014/0257445 A1 | 9/2014 | Weber et al. | |
| 2016/0030732 A1* | 2/2016 | Weber | ............ A61L 31/10 |
| | | | 427/2.1 |

FOREIGN PATENT DOCUMENTS

| | | |
|---|---|---|
| JP | 2007500038 A | 4/2012 |
| JP | 2012509140 A | 4/2012 |
| WO | WO2010033909 A2 | 3/2010 |

OTHER PUBLICATIONS

Cha, T.-W et al., Immobilization of oligonucleotides on poly(ethylene glycol) brush-coated Si surfaces, Science Direct, 2002, pp. 26-32.

Choi, Won Mook et al., Compressed-carbon dioxide (CO2) assisted nanoimprint lithography using polymeric mold, Science Direct, 2005, pp. 1957-1960.

International Preliminary Report on Patentability issued in PCT/US2014/020566, dated Sep. 17, 2015, 8 pages.

International Search Report and Written Opinion issued in PCT/US2014/020566, dated Jun. 24, 2014, 10 pages.

Minko, Sergiy, Responsive polymer brushes, Journal of Macromolecular Science, Part C: Polymer Reviews, 46, 2006, pp. 397-420.

International Search Report and Written Opinion issued in PCT/US2016/050669, dated Nov. 30, 2016, 11 pages.

* cited by examiner

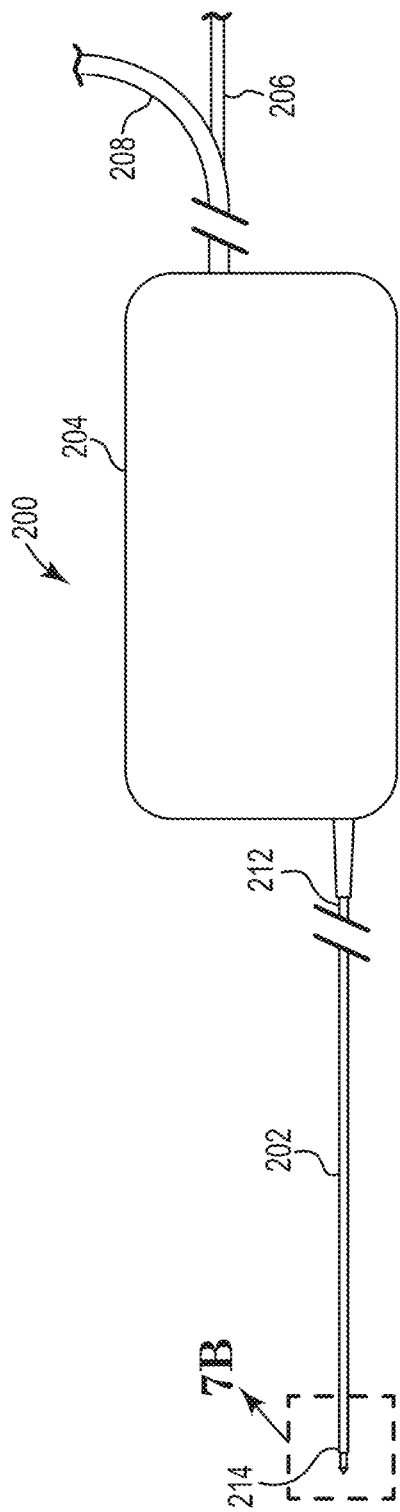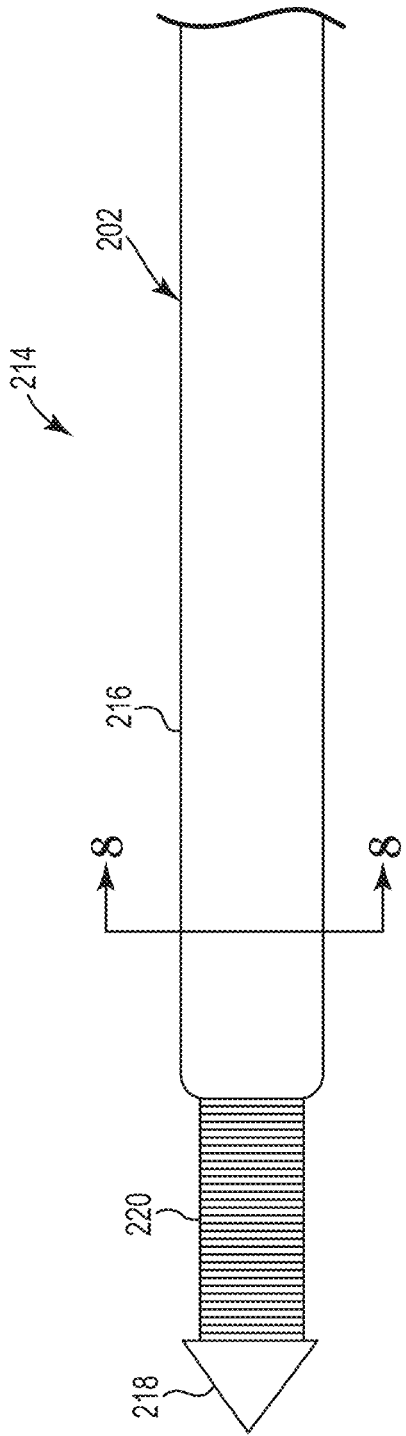

MEDICAL DEVICE WITH A STRUCTURED COATING

CROSS-REFERENCE TO RELATED APPLICATIONS

This application is a continuation-in-part of U.S. application Ser. No. 14/197,559, filed Mar. 4, 2014, which claims the benefit under 35 U.S.C. §119(e) to U.S. Provisional Application 61/773,471, entitled "PACING LEADS WITH A STRUCTURED COATING", filed on Mar. 6, 2013, which are herein incorporated by reference in their entirety.

TECHNICAL FIELD

The present invention relates to a medical device having a coating, and more particularly, to a medical device having a coating containing microstructures for reducing wear. Methods of making such coatings are also provided.

BACKGROUND

Medical devices may include a tubular body including a lumen and a wire extending through the tubular body. For example, a lead includes at least one wire—a lead wire, extending through a tubular body—a lead body. The lead wire may be metallic while the lead body may be a silicone or polyurethane material. The lead body isolates the lead wires from surrounding tissue and any external environment that could compromise the lead's performance.

During use, lead wires may rub on the inner surface of the lead body due to the constant movement of the patient. Over time, the lead wires may abrade or wear on the inner surface of the lead body. In some circumstances, such wear can result in a failure of the isolation system and short-circuiting of the lead.

In another example, a rotational atherectomy catheter includes at least one wire—a drive shaft, extending through a tubular body—a catheter. The drive shaft may be a helically coiled metallic wire while the catheter may be a silicone or polyurethane material. The catheter isolates the rotating drive shaft from the surrounding tissue. A lubricant including saline may flow between the catheter and the drive shaft.

During use, where the catheter must curve to confirm to the human body, the drive shaft may be forced against the inner surface of the catheter. This force may push lubricant out from between the outer surface of the drive shaft and the inner surface of the catheter. Without lubrication, friction between the rotating drive shaft and the catheter may generate head and particles which may result in a failure of the rotational atherectomy catheter.

SUMMARY

Disclosed herein are various embodiments of a coated medical device, as well as methods for coating medical devices.

Example 1 is a medical device including a catheter having a distal end and a proximal end, a lumen extending through the catheter from the distal end to the proximal end, a drive shaft extending through the lumen from the distal end to the proximal end, and a polymeric coating. The drive shaft is a helically coiled wire and has an outer surface. The polymeric coating is on at least a portion of the outer surface of the wire. The coating comprises a bulk material and a plurality of flexible microstructures disposed on the bulk material. The microstructures extend outwardly from a surface of the polymeric coating.

In Example 2, the medical device of Example 1, wherein the flexible microstructures include a first end and a second end, and the distance from the first end to the second end is from 5 micrometers to 100 micrometers.

In Example 3, the medical device of either of Examples 1 or 2, wherein the microstructures are integral with the polymeric coating.

In Example 4, the medical device of any of Examples 1-3, wherein the coating includes at least one member selected from the group consisting of ethylene tetrafluoroethylene (ETFE) and polyethylene terephthalate (PET).

In Example 5, the medical device of any of Examples 1-4, further comprising a protective coating on at least a portion of the flexible microstructures.

In Example 6, the medical device of Example 5, wherein the protective coating has a thickness of 3 nanometers to 30 nanometers.

In Example 7, the medical device of either of Examples 5 or 6, wherein the protective coating has a higher modulus of elasticity than the polymeric coating.

In Example 8, the medical device of any of Examples 1-7, further comprising a lubricant between at least a portion of an inner surface of the tubular body and at least a portion of the microstructures.

Example 9 is medical device including a tubular body having a distal end and a proximal end and including at least one lumen and at least one inner surface extending from the distal end to the proximal end, a wire extending through the at least one lumen and having an outer surface, and a polymeric coating. The polymeric coating is disposed on at least a portion of the outer surface of the wire. The polymeric coating includes a bulk material and a plurality of flexible microstructures disposed on the bulk material. The microstructures extend outwardly from a surface of the polymeric coating and have at least one point of contact with the inner surface of the tubular body.

In Example 10, the medical device of Example 9, wherein the microstructures are integral with the polymeric coating.

In Example 11, the medical device of either of Examples 9 or 10, wherein the microstructures can bend at least 0.0015 radians.

In Example 12, the medical device of any of Examples 9-11, wherein the microstructures have a minimum diameter and a length that is at least twice the minimum diameter.

In Example 13, the medical device of any of Examples 9-12, further comprising a protective coating on at least a portion of the flexible microstructures.

In Example 14, the medical device of Example 13, wherein the protective coating has a higher modulus of elasticity than the polymeric coating.

In Example 15, the medical device of any of Examples 9-14, wherein the tubular body is a catheter and the wire is a drive shaft.

Example 16 is a method of forming a medical device. The method includes forming a polymeric coating on an outer surface of a wire, exposing the polymeric coating to laser energy at a fluence level below the ablation threshold to form a plurality of flexible microstructures extending outward from a surface of the coating, and positioning the wire within a lumen of a tubular body.

In Example 17, the method of Example 16, wherein the laser energy is a polarized pulsed laser irradiation.

In Example 18, the method of either of Examples 16 or 17, further including applying a protective coating on at least a portion of the flexible microstructure.

In Example 19, the method of any of Examples 16-18, further including dispensing a lubricant between the microstructures and the tubular body.

In Example 20, the method of any of Examples 16-19, wherein the tubular body is a catheter and the wire is a drive shaft.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 7A and 7B illustrate another exemplary embodiment of a medical device.

Figure 1:
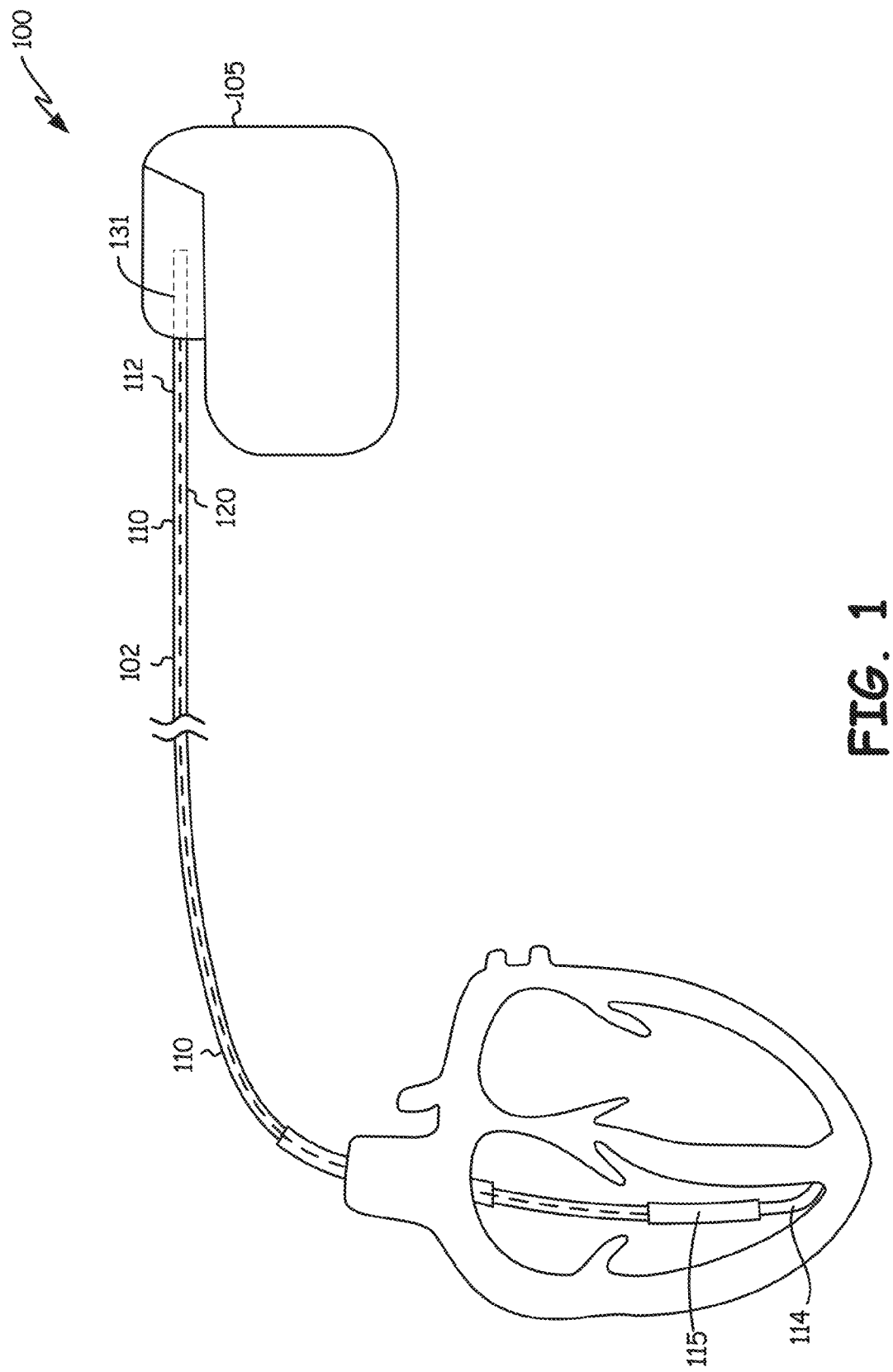
FIG. 1 illustrates an exemplary embodiment of a medical device.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 illustrates an implantable medical device 100, such as a lead 102 for use with a pulse generator 105. The lead 102 includes a lead body 110, and at least one elongate conductor 120 contained within the lead body 110. The lead body 110 is a tubular body that extends from a proximal end 112 to a distal end 114. The proximal end 112 of the lead 102 is electrically coupled with the pulse generator 105, for example, with a terminal pin 131.

The medical device 100 generically represents, but is not limited to, cardiac function management (referred to as "CFM") systems such as pacers, cardioverters/defibrillators, pacers/defibrillators, biventricular or other multi-site resynchronization or coordination devices such as cardiac resynchronization therapy (referred to as "CRT") devices, sensing instruments, drug delivery systems, neurostimulation devices, or organ stimulation devices. Thus, the medical device 100 can be utilized for any application that delivers a product, such as an electrical shock or pulse or a drug.

The optional pulse generator 105 includes a source of power as well as electronic circuitry (not shown). In some embodiments, the electronic circuitry can include one or more microprocessors that provide processing and/or evaluation functions, and that can determine and deliver electrical shocks or pulses of different energy levels and timing. The pulse generator can be employed as part of a variety of useful therapies, including for neurostimulation or ventricular defibrillation or cardioversion. It can also be used to pace the heart in response to one or more sensed cardiac arrhythmia including fibrillation, cardiac resynchronization, tachycardia, or bradycardia. In some embodiments, the pulse generator 105 can be powered by one or more batteries, though any other internal or external power source may be used for the given application. In some embodiments, the pulse generator 105 can sense intrinsic signals of the heart and generate a series of timed electrical discharges.

The medical device 100 may further include one or more electrodes 115. The one or more electrodes 115 are each electrically coupled with the at least one conductor 120. The electrode 115 allows for electrical signals to be delivered from the pulse generator 105 to the target tissue or location.

The lead body 110 is designed to separate and isolate electrically conductive components within the lead body 110 from surrounding tissues of the patient. Even under ordinary and expected conditions, once implanted in a human body, the conductive components can rub against and wear the inner surface of the lead body 110. Over time, this repeated wearing can result in failure of the isolation, which in turn can result in short circuiting. In some embodiments described herein, the electrically conductive components include a coating which may reduce wear.

Figure 2:
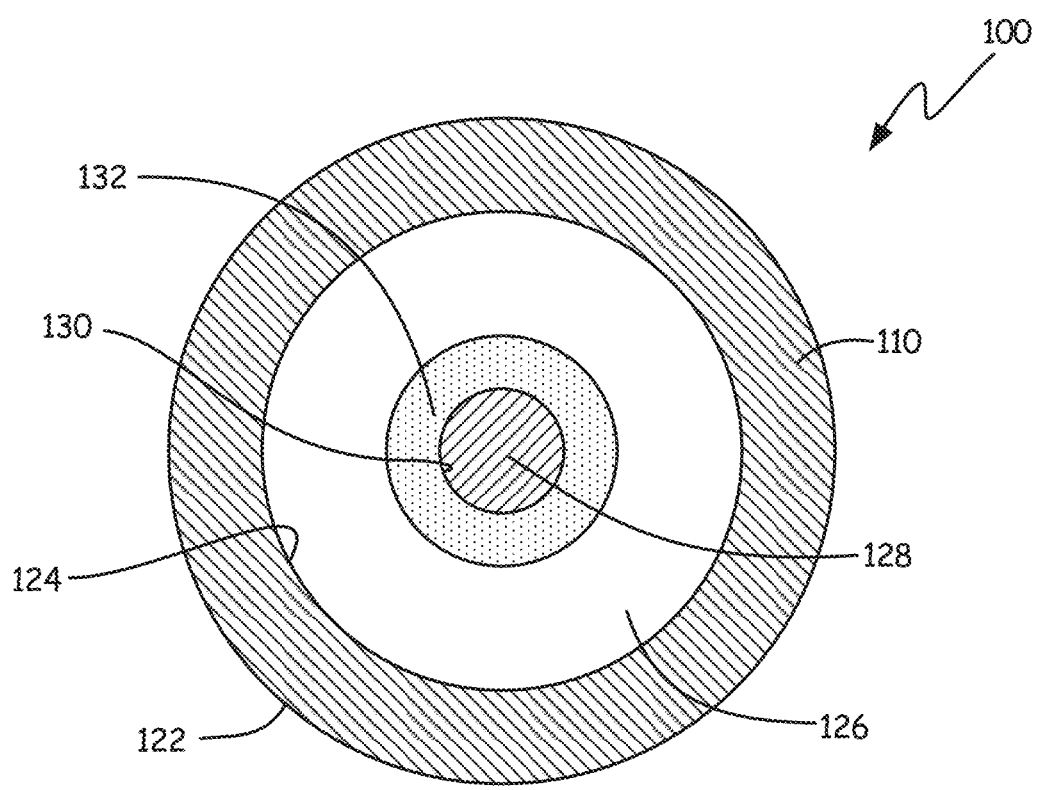
FIG. 2 illustrates an exemplary cross-sectional view of the medical device of FIG. 1.

FIG. 2 illustrates a cross-sectional view of an embodiment of the medical device 100 which includes a lead body 110 (having an outer surface 122, an inner surface 124, and a lumen 126), a lead wire 128 having an outer surface 130, and a polymeric coating 132. Although the polymeric coating 132 is illustrated schematically as having a smooth surface, the polymer coating 132 includes a plurality of microstructures which extend generally outward from a surface of the polymer coating 132 towards the inner surface 124 of the lead body 110.

The lead body 110 is generally flexible, but substantially non-compressible along its length. The lead body 110 may have any suitable cross-sectional shape. For example, in some embodiments, the lead body 110 may have a substantially circular cross-section. The lead body 110 may be of any suitable size for implantation. In some embodiments, the lead body 110 may have a substantially circular cross-section and the outer diameter of the lead body 110 may range between about 0.6 millimeters (mm) and about 5 mm.

The lead body 110 can isolate the lead wire 128 from the surrounding tissue or environment. The lead body 110 may include a suitable bio-compatible, electronically insulative material. For example, in some embodiments, the lead body 110 may include silicone or a polyurethane. In some embodiments, the lead body 110 may have a substantially uniform composition along its length. In other embodiments, the composition of the lead body 110 may vary in any direction, including along the length and/or thickness.

The lead body 110 can include one or more channels or lumens 126 extending axially through the lead body 110 from the proximal end to the distal end of the lead body 110. The lumen 126 forms the inner surface 124 of the lead body 110. The lumen 126 can have any suitable cross-sectional shape, such as a substantially circular, rectangular, or triangular cross-sectional shape. The lumen 126 can have a substantially uniform cross-sectional area or the cross-sectional area may vary along the length of the lumen 126 (or the lead body 110).

One or more lead wires 128 can extend through the one or more lumens 126. In some embodiments, the lead wire 128 may extend from the proximal end to the distal end of the lead body 110. For example, the lead wire 128 may be parallel with a longitudinal axis of the lead body 110.

The lead wire 128 is conductive and may include any suitable conductive material. For example, in some embodiments, the lead wire 128 may be metallic.

The polymeric coating 132 may completely surround or may cover any portion of the outer surface 130 of the lead wire 128. The polymeric coating 132 is positioned between the outer surface 130 of the lead wire 128 and the inner surface 124 of the lead body 110. As described herein, the polymeric coating 132 may decrease friction between the lead wire 128 and the inner surface 124. Additionally or alternatively, the polymeric coating 132 may reduce wear on the inner surface 124 of the lead body 110.

Suitable materials for the polymeric coating 132 include materials that reduce the wear on the lead body 110. For example, suitable polymeric materials for the polymeric coating 132 may include rubber (natural, butyl, silicone), polyamides such as nylon, polyesters such as Mylar, polypropylene (PP), polystyrene (PS), polyvinyl chloride (PVC), polymethylmethacrylate (PMMA), polycarbonate (PC), polytetrafluoroethylene (PTFE), polyethylenes (PE) such as low-density PE (LDPE), medium-density PE (MDPE), high-density PE (HDPE), and cross-linked PE (XLPE), ethylene tetrafluoroethylene (ETFE) and polyethylene terephthalate (PET). In some embodiments, the polymeric coating 132 may have a higher modulus of elasticity than the lead body 110, e.g., the polymeric coating 132 may be made of a material that is harder than that of the lead body 110.

Figure 3:
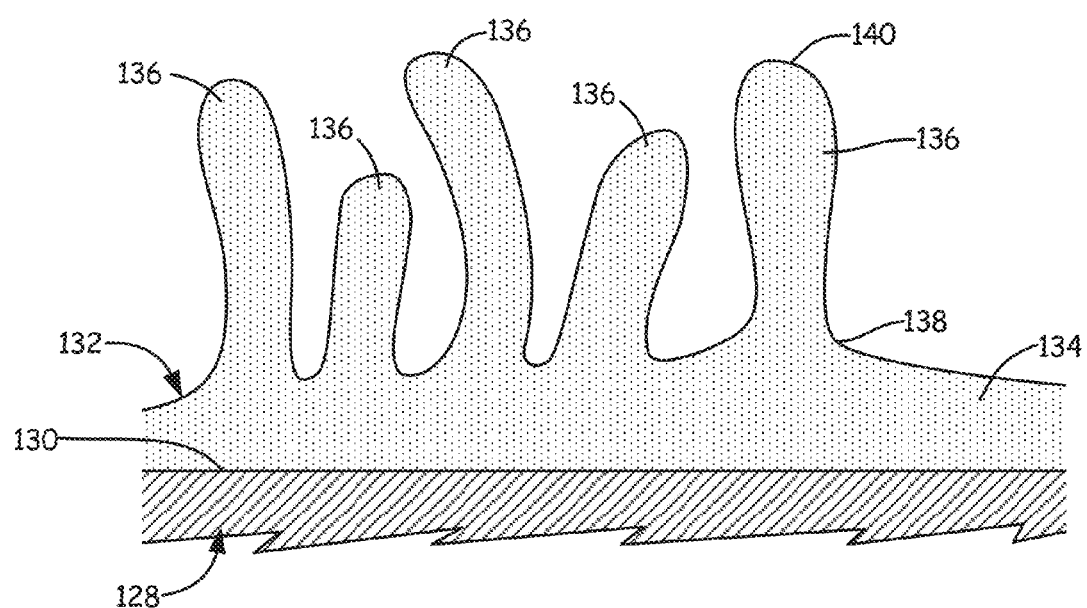
FIG. 3 is a schematic of an exemplary coating.

FIG. 3 is a schematic drawing of an exemplary polymeric coating 132 on the outer surface 130 of the lead wire 128 and including bulk or base material 134 and one or more microstructures or hairs 136 having first or bulk ends 138 and second or tip ends 140. The bulk material 134 may be directly adjacent to the outer surface 130 of the lead wire 128. Alternatively, one or more intermediary materials or layers may be positioned between the polymeric coating 132 and the outer surface 130 of the lead wire 128.

The microstructures 136 may be three-dimensional objects that generally extend outwardly from the polymeric coating 132 (and indirectly from the outer surface 130 of the lead wire 128.) In some embodiments, the microstructures 136 may resemble "pillars" or "hairs" extending from the bulk 134 of the polymeric coating 132 on the lead wire 128.

The bulk ends 138 of the microstructures 136 may be adjacent the bulk material 134 and the tip ends 140 may be opposite the bulk ends 138. For example, the bulk ends 138 may be closer to the outer surface 130 of the lead wire 128 than the tip ends 140.

In some embodiments, the microstructures 136 and the bulk material 134 may have a unitary construction. For example, the microstructures 136 and the bulk material 134 can be integral. Alternatively, the microstructures 136 and the bulk material may be separate structures.

The location of the microstructures 136 on the bulk material 134 may be random or may form a pattern or an array. For example, the microstructures 136 may be positioned in a random pattern by treating the polymeric material 132 with a laser. In some embodiments, the maximum cross-sectional area of the connecting area between the bulk material 134 and the microstructures 136 is smaller than about $\frac{1}{10}^{th}$ of the total surface area of the microstructures 136. That is, in some embodiments, the maximum cross-sectional area of the bulk ends 138 which connect the microstructures 136 to the bulk material 134 may be less than about $\frac{1}{10}^{th}$ of the total surface area of the microstructures 136.

The microstructures 136 may have any number of cross-sectional shapes, where cross-section refers to a cross-section taken generally parallel to the bulk material 134 of the polymeric coating 132. For example, the microstructures 136 may have a generally rectangular or triangular cross-sectional shape. In some embodiments, the microstructures 136 may have a generally circular cross-sectional shape, which may enable the microstructures 136 to bend in all directions perpendicular to the surface of the bulk material 134.

The microstructures 136 may have a substantially uniform cross-sectional area along the length or the cross-sectional area may vary along the length of the microstructures 136. For example, the cross-sectional area of a microstructure 136 may increase and then decrease along a perpendicular vector away from a surface of the polymeric coating 132 (e.g., a surface of bulk material 134) thereby creating a bulge. The bulge may be at the tip end 140 and/or at a location between the bulk end 138 and the tip end 140.

The microstructures 136 may have a maximum cross-sectional thickness or diameter from about 5 micrometers (um) to about 50 um, from about 5 um to about 25 um, from about 5 um to about 20 um or from about 5 um to about 15 um.

The microstructures 136 may also have a minimum cross-sectional thickness or diameter, which may be the same or different than the maximum cross-sectional thickness or diameter. Suitable minimum cross-sectional thicknesses or diameters for the microstructures 136 may be from about 2.5 um to about 50 um, from about 5 um to about 25 um or from about 5 um to about 10 um.

The length or height of a microstructure 136 can be measured from the bulk end 138 to the tip end 140. In some embodiments, the microstructures 136 can be any suitable length that serves to reduce friction between the lead wire 128 and the lead body 110. Additionally, the length of the structures can be any suitable length that maintains the lead body 110 within a useful thickness or diameter. In some embodiments, the length of a microstructure 136 may be at least twice as long as the minimum diameter or thickness of the microstructure 136.

In some embodiments, the length of the microstructures 136 can be on the micrometer scale. For example, the length of the microstructures 136 can range between about 5 um and about 100 um. Alternatively, the microstructures 136 can have a length of about 10 um to about 50 um. In a still further alternative, the microstructures 136 can have a length of about 20 um to about 30 um.

In some embodiments, the microstructures 136 may be elastic or flexible. For example, the microstructures 136 may individually bend, flex or move similar to the bristles of a toothbrush. The ability or degree to which the microstructures 136 can bend depends on, among other factors, the polymeric material of the microstructures 136 and/or the thickness or diameter of the microstructures 136. In some embodiments, the microstructures 136 may be spaced so that the microstructures 136 can bend a minimum of 0.0015 radians without touching an adjacent microstructure 136.

In some embodiments, the lead wire 128 including the polymeric coating 132 having the microstructures 136 may be positioned within the lead body 110, and the microstructures 136 may extend outwardly from the bulk material 134 towards the inner surface 124 of the lead body 110. In some embodiments, the microstructures 136 may contact the inner surface 124 of the lead body 110, and the microstructures 136 may individually bend or move during such contact. For example, the lead wire 128 including the polymeric coating 132 having the microstructures 136 may be positioned within the lead body 110 such that at least one of the microstructures 136 extends outwardly from the bulk material 134 (and indirectly from the lead wire 128) and has at least one point of contact with the inner surface 124 of the lead body 110.

While not wishing to be bound by any particular theory, it is believed that the microstructures 136 of the polymeric coating 132 may reduce the wear or abrasion caused by the lead wire 128 on the lead body 110. For example, the flexibility of the microstructures 136 may reduce the friction created between the lead wire 128 and the lead body 110, thus reducing wear on the inner surface 124 of the lead body 110. The microstructures 136 may also have a reduced contact surface area with the inner surface 124 as compared to the contact surface area between the lead wire 128 without the polymeric coating 132 and the inner surface 124, which may also reduce wear on the inner surface 124.

Figure 4A:
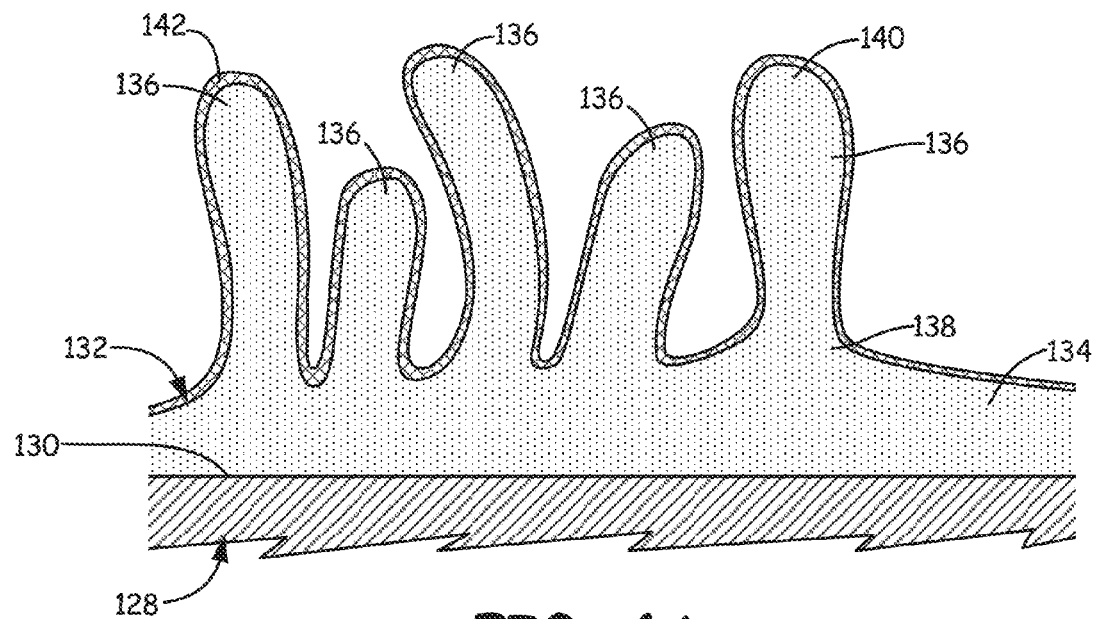
FIG. 4A and FIG. 4B are schematics of alternative exemplary coatings.

As shown in FIG. 4A, in some embodiments, a protective coating 142 may cover all or at least a portion of polymeric coating 132. In some embodiments, the protective coating 142 may have a higher modulus of elasticity than the polymeric coating 132. That is, the polymeric coating 132 may be more flexible than the protective coating 142. Additionally or alternatively, the protective coating 142 may be more resistive to wear from contact with the inner surface 124 as compared to the polymeric coating 132.

In some embodiments, the microstructures 136 including the protective coating 142 are flexible. That is, in some embodiments, the microstructures 136 including the protective coating 142 can bend, flex or move when they contact the inner surface 124 of the lead body 110. The ability or degree to which the microstructures 136 can flex depends on the thickness and material of the polymeric coating 132 and the protective coating 142, among other factors.

The protective coating 142 may protect the microstructures 136 when the microstructures 136 contact the inner surface 124 of the lead body 110. For example, the protective coating 142 may reduce the likelihood that the microstructures 136 are damaged or break during contact with the lead body 110. In some embodiments, the protective coating 142 may protect the microstructures 136 from damage due, at least in part, to the higher modulus of elasticity of the protective coating 142.

Additionally, the protective coating 142 may fill defects or cracks, such as micro- or nano-size cracks, in the polymeric coating 132, which otherwise could be an originating location for larger cracks and damage to the polymeric coating 132.

Suitable materials for protective coating 142 may include a ceramic or a polymeric material. In certain embodiments, suitable materials for the protective coating 142 include polyamides. In other embodiments, suitable materials for the protective coating include aluminum oxide and polyurethanes.

In some embodiments, the protective coating 142 may have a thickness that reduces damage experienced by the microstructures 136 during contact with lead body 110 while still enabling the microstructures 136 to be flexible (e.g., to bend, flex or move). In some embodiments, the protective coating 142 may have a thickness of about 75 nanometers or less. For example, in some embodiments, the protective coating 142 may have a thickness of about 5 nanometers (nm) to about 75 nm. In other embodiments, the protective coating 142 may have a thickness of about 5 nm to about 50 nm. In still further embodiments, the protective coating 142 may have a thickness of about 5 nm to about 10 nm.

Ceramic layers having a thickness of greater than 30 nm may have an increased probability of cracking or breaking. When protective coating 142 includes a ceramic material, the protective coating 142 may have a thickness of about 30 nanometers or less. For example, in some embodiments, the protective coating 142 may have a thickness of about 3 nanometers (nm) to about 30 nm. In other embodiments, the protective coating 142 may have a thickness of about 5 nm to about 20 nm. In still further embodiments, the protective coating 142 may have a thickness of about 5 nm to about 10 nm.

In some embodiments, a lubricant may be present between the inner surface 124 of the lead body 110 and the polymeric coating 132 or protective coating 142. For example, the lubricant may be dispersed in the lumen 126.

The lubricant may be any suitable material that reduces friction. For example, the lubricant may reduce friction between the inner surface 124 of the lead body 110 and the polymeric coating 132 or protective coating 142. In some embodiments, suitable lubricants include silicon oil, fluorosilicone oil, and polyethylene glycol (PEG) with a molecular weight less than about 600 g/mol.

The lubricant may further reduce wear on the inner surface 124 of the lead body 110, for example by reducing the friction between the inner surface 124 of the lead body 110 and the polymeric coating 132 or protective coating 142. In some embodiments, the microstructures 136 may provide a porous structure which may retain at least a portion of the lubricant. The microstructures 136 may also assist with maintaining dispersion of the lubricant among the length of the lead body 110 and the lead wire 128.

In some embodiments, the polymeric coating 132 and/or the protective coating 142 may also provide a porous structure which may retain at least a portion of the lubricant.

Figure 4B:
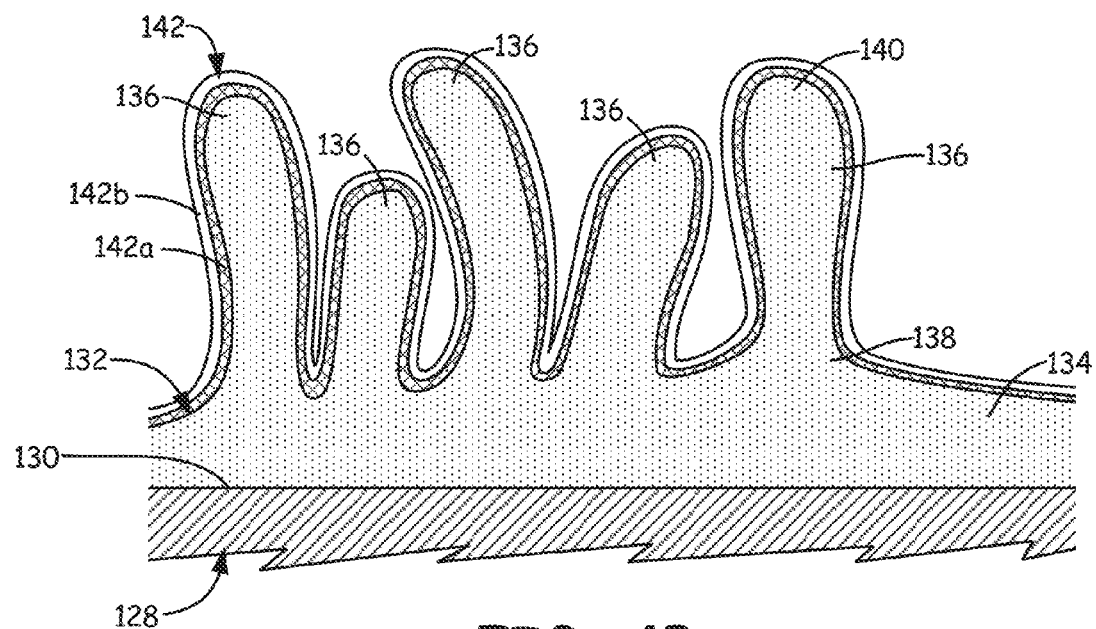

FIG. 4B illustrates an alternative, hybrid, protective coating 142 which includes two or more layers of different materials. For example, the hybrid protective coating 142 may include two or more layers of ceramic material, two or more layers of polymeric material and/or alternating layers of ceramic material and polymeric material. For example, the hybrid protective coating 142 may include a ceramic layer 142a adjacent to the polymeric coating 132 and a polymeric layer 142b adjacent the ceramic layer 142a.

The hybrid protective coating 142 may be formed by an atomic layer deposition process in which the precursors are switched to change the deposited layer. In some embodiments, ceramic layers having a thickness greater than 30 micrometers may have a greater probability of cracking due at least in part to the low flexibility of ceramic materials. Alternating ceramic and polymeric material embeds the less flexible ceramic material in a flexible polymer layer, and may enable the protective coating 142 to be greater than about 30 micrometers thick, while the ceramic layer(s) 142a of the protective coating 142 may individually have a thickness of about 30 micrometers or less. Suitable organic-inorganic combinations for protective coating 142 include polyamide-polyimide combinations.

Figure 5:
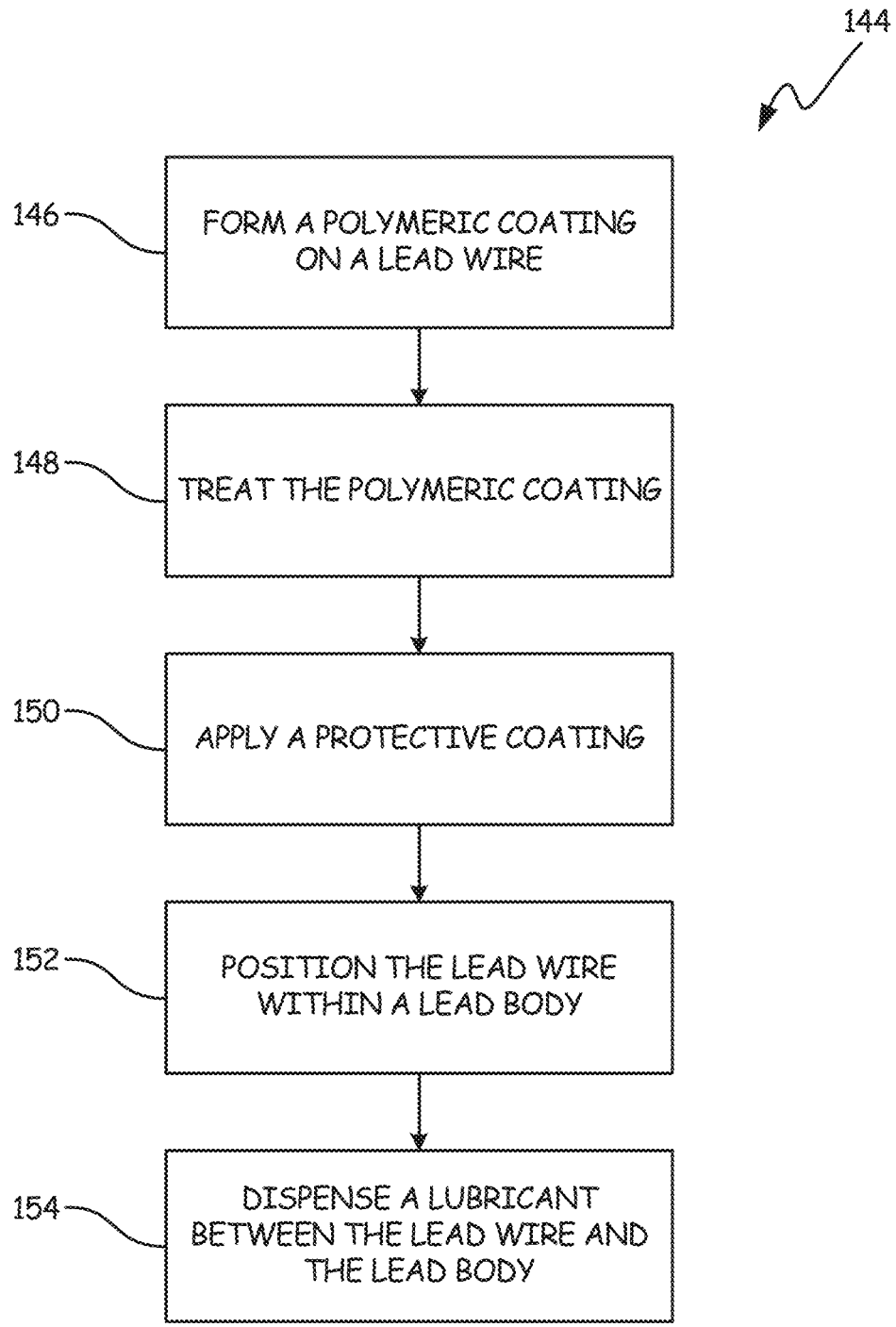
FIG. 5 is an exemplary method for forming an exemplary coating.

An exemplary method 144 for forming the medical device 100 having a polymeric coating 132 including microstructures 136 is illustrated in the block diagram of FIG. 5, which includes forming a polymeric coating on a lead wire (block 146), treating the polymeric coating (block 148), optionally applying a protective coating (block 150), positioning the lead wire within a lead body (block 152), and optionally dispensing a lubricant between the lead wire and the lead body (block 154).

The polymeric coating may be formed on the lead wire using a variety of known techniques (block 146). In one embodiment, the polymeric coating may be formed on the lead wire by brush coating, spray coating, or dip coating, followed by a curing process. In certain embodiments, the polymeric coating may have a thickness of about 5 um to about 100 um. In other embodiments, the polymeric coating may have a thickness from about 10 um to about 50 um or from about 20 um to about 30 um.

Figure 6:
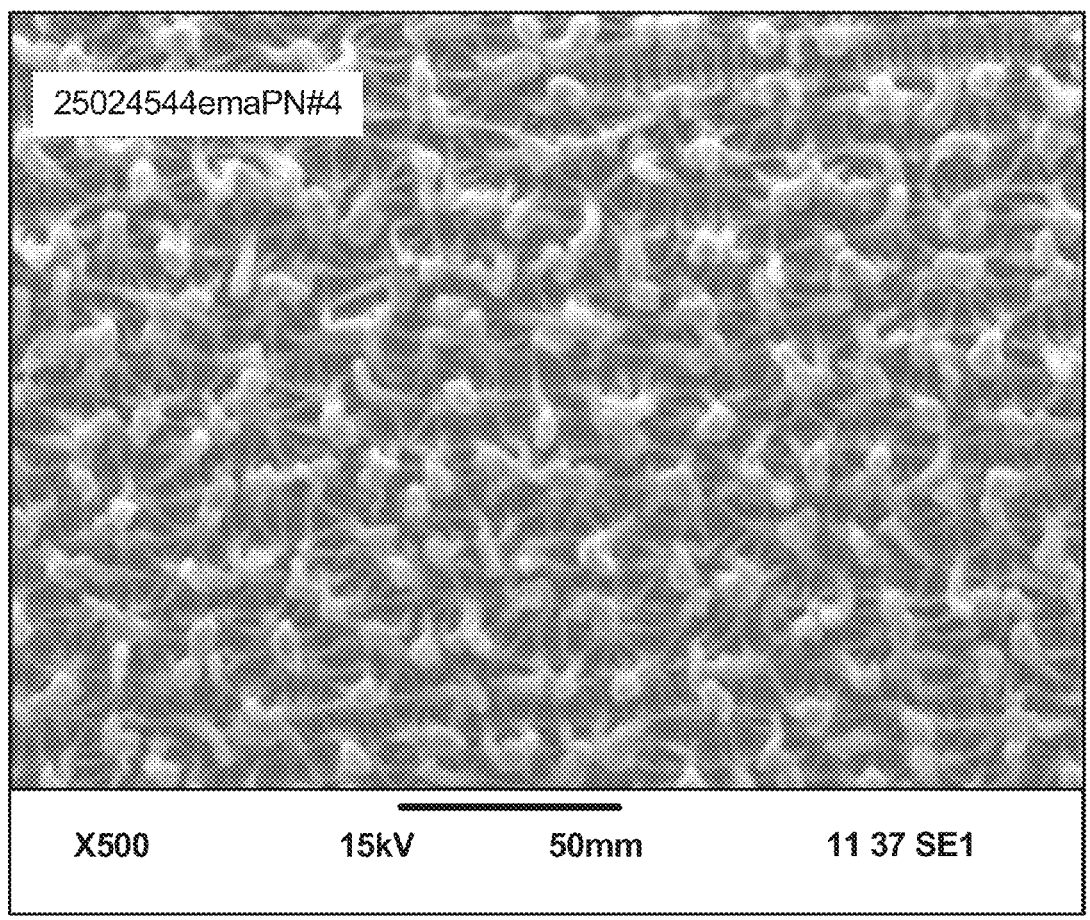
FIG. 6 is a scanning electron microscope image of laser induced periodic surface structures.

The polymeric coating may be treated to form the microstructures or hairs (block 148). In some embodiments, the microstructures, or hairs, can be formed on the polymeric coating using known techniques. For example, the polymeric coating may be treated with a laser treatment. In some embodiments, the polymeric coating may be exposed to laser energy in order to provide a coating characterized by the microstructures described herein. The size and shape of the microstructures can be controlled by selecting the laser parameters such as wavelength, fluence, and exposure time. In some embodiments, a suitable laser treatment may include polarized pulsed laser irradiation at fluence levels below the ablation threshold of the polymeric coating, and may produce microstructures, which may also be referred to as laser induced periodic surface structures (LIPSS). During the polarized pulsed laser irradiation, the polymer is melted very briefly during nano-second pulses. The electric field (which is in one direction because of the polarization) causes a small percentage of the polymer dipole segments to align themselves with the field during the phase. Repeated laser pulsing gives an incremental effect and can cause the majority of the polymer dipole segments to align. In certain embodiments, a suitable wavelength of the laser is 196 nm, 356 nm or other conventional laser frequencies. FIG. 6 is a scanning electron microscope image of exemplary LIPSS or microstructures.

In other embodiments, the microstructures can be formed on the polymeric coating by use of suitable printing process, such as a compressed carbon dioxide assisted nanoimprint lithography technique. For example, a mold may be placed over the polymeric coated lead wire. The mold may be depressed using compressed carbon dioxide in a pressure chamber to form flexible microstructures on the surface of the lead wire.

An optional protective coating may be applied to the polymeric coating after formation of the microstructures (block 150). As described herein, the protective coating may include a ceramic material, a polymeric material or alternating layers of ceramic and polymeric materials. In certain embodiments, the protective coating may have a thickness of about 30 nm or less, 20 nm or less or 10 nm or less. Exemplary methods for forming the protective coating include atomic layer deposition (ALD) and molecular layer deposition (MLD). These techniques allow deposition of one atomic or molecular layer at a time and may form a conformal coating. In some embodiments, the protective coating may have a smoother surface than the underlying polymeric coating, which results in the microstructures having a smoother topography. Alternatively, the protective coating may be applied to the polymeric coating before the formation of the microstructures.

The lead wire, including the polymeric coating having microstructures, and optionally including the protective coating, can be positioned within a lead body (block 152). In certain embodiments, the lead wire is positioned in a lumen running axially through the lead body (e.g., from the distal end to the proximal end of the lead body). The polymeric coating is located between the inner surface of the lead body and the outer surface of the lead wire and may reduce friction between and/or wear from contact between the lead body and the lead wire.

A lubricant may optionally be dispensed between the lead wire and the lead body (item 154). The microstructures formed on the lead wire may assist in maintaining the lubricant dispersed along the length of the lead wire. In some embodiments, the microstructures may drag the lubricant along, pushing it into narrow spaces. In certain embodiments, the lubricant may further reduce friction between the inner surface of the lead body and the lead wire, and may reduce wear or abrasion on the inner surface of the lead body from the lead wire.

FIGS. 7A and 7B illustrate another exemplary embodiment of a medical device. FIG. 7A illustrates a medical device 200, such as a rotational atherectomy device 202 for use with a housing 204. The housing 204 may include a drive connection 206, a fluid supply line 208, and a rotational drive device, such as a motor or turbine (not shown). The drive connection 206 may be an electrical connection, a compressed gas connection, or other connection necessary to drive the rotational drive device. The fluid supply line 208 may supply a biocompatible cooling and lubricating solution, for example, saline. The rotational atherectomy device 202 extends from a proximal end 212 to a distal end 214.

FIG. 7B shows a magnified portion of the distal end 214 of the rotational atherectomy device 202. FIG. 7B shows that the rotational atherectomy device 202 may include a catheter 216, a cutting section 218, and a drive shaft 220. The catheter 216 is a tubular body including a lumen 226 (FIG. 8) that extends from the proximal end 212 to the distal end 214. The cutting section 218 is a device for cutting, abrading, or otherwise removing tissue. The cutting section 218 may include a plurality of blades, a burr, or other cutting or abrading devices or materials known in the art. In some embodiments, the drive shaft 220 may be formed of a helically coiled wire including a lumen. In other embodiments, the drive shaft 220 may be a straight wire. The drive shaft 220 is connected to the cutting section 218 and may extend through the lumen 226 of the catheter 210 from the proximal end 212 to the distal end 214.

Considering FIGS. 7A and 7B together, the proximal end 212 of the rotational atherectomy device 202 may connect to the housing 204 to physically connect the rotational drive device within housing 204 to the drive shaft 220, and to fluidly connect the fluid supply line 208 to the catheter 216.

In operation, the distal end 214 of the rotational atherectomy device 202 may be inserted into a blood vessel of a patient suffering from, for example, the formation of calcified atherosclerotic plaque deposits on the walls of the blood vessel, known as atherosclerosis. The rotational drive device within the housing 204 may cause the drive shaft 220 to rotate within the catheter 210, thus rotating the connected cutting section 218 at the distal end 214. The distal end 214 may be maneuvered to the site of the deposit, where the rotating cutting section 218 may abrade, or cut away, the offending deposit. The catheter 216 may be flushed by the fluid supplied by the fluid supply line 208 to cool and lubricate the drive shaft 220 as it rotates within the catheter 216.

Figure 8:
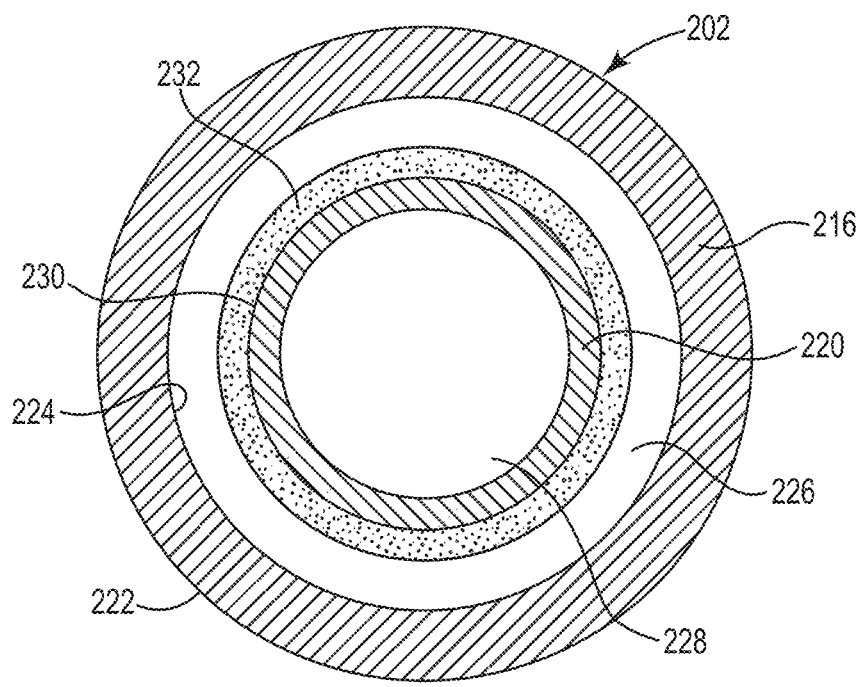
FIG. 8 illustrates an exemplary cross-sectional view of the medical device of FIGS. 7A and 7B.

FIG. 8 illustrates an exemplary cross-sectional view of the of the rotational atherectomy device 202 of FIGS. 7A and 7B. As shown in FIG. 8, the catheter 216 includes an outer surface 222 and an inner surface 224. The inner surface 224 defines the lumen 226. The drive shaft 220 may include an inner lumen 228 and an outer surface 230. The rotational atherectomy device 220 includes a polymeric coating 232 formed on the outer surface 230 of the drive shaft 220. Although the polymeric coating 232 is illustrated schematically as having a smooth surface, the polymer coating 232 includes a plurality of microstructures which extend generally outward from a surface of the polymer coating 232 towards the inner surface 224 of the catheter 216.

The catheter 216 can isolate the drive shaft 220 from the surrounding tissue or environment. The catheter 216 may include a suitable flexible bio-compatible material. For example, in some embodiments, the catheter may include high-density polyethylene, polyamide, silicone or polyurethane. In some embodiments, the catheter 216 may have a substantially uniform composition along its length. In other embodiments, the composition of the catheter 216 may vary in any direction, including along the length and/or thickness.

The polymeric coating 232 may completely surround or may cover any portion of the outer surface 230. The polymeric coating 232 is positioned between the outer surface 230 of the drive shaft 220 and the inner surface 224 of the catheter 216. As described herein, the polymeric coating 232 may decrease friction between the drive shaft 220 and the inner surface 224. Additionally or alternatively, the polymeric coating 232 may reduce wear on the inner surface 224 of the catheter 216.

The polymeric coating 232 may be identical to the polymeric coating 132 described above in reference to FIG. 3, including bulk or base material 134 and one or more microstructures or hairs 136 having first or bulk ends 138 and second or tip ends 140. Suitable materials for the polymeric coating 232 may include rubber (natural, butyl, silicone), polyamides such as nylon, polyesters such as Mylar, polypropylene (PP), polystyrene (PS), polyvinyl chloride (PVC), polymethylmethacrylate (PMMA), polycarbonate (PC), polytetrafluoroethylene (PTFE), polyethylenes (PE) such as low-density PE (LDPE), medium-density PE (MDPE), high-density PE (HDPE), and cross-linked PE (XLPE), ethylene tetrafluoroethylene (ETFE) and polyethylene terephthalate (PET). In some embodiments, the polymeric coating 232 may have a higher modulus of elasticity than the catheter 216, e.g., the polymeric coating 232 may be made of a material that is harder than that of the catheter 216.

In some embodiments, the drive shaft 220 with the polymeric coating 232 having the microstructures 136, may be positioned within the catheter 216, and the microstructures 136 may extend outwardly from the bulk material 134 towards the inner surface 224 of the catheter 216. In some embodiments, the microstructures 136 may contact the inner surface 224 of the catheter 216, and the microstructures 136 may individually bend or move during such contact. For example, the drive shaft 220, including the polymeric coating 132 having the microstructures 136, may be positioned within the catheter 216 such that at least one of the microstructures 136 extends outwardly from the bulk material 134 (and indirectly from the drive shaft 220) and has at least one point of contact with the inner surface 224 of the catheter 216.

While not wishing to be bound by any particular theory, it is believed that the microstructures 136 of the polymeric coating 232 may reduce the wear or abrasion caused by the drive shaft 220 on the catheter 216. For example, the flexibility of the microstructures 136 may reduce the friction created between the drive shaft 220 and the catheter 216, thus reducing wear on the inner surface 224 of the catheter 216. The microstructures 136 may also have a reduced contact surface area with the inner surface 224 as compared to the contact surface area between the catheter 216 without the polymeric coating 232 and the inner surface 224, which may also reduce wear on the inner surface 224.

It is also believed that the microstructures 136 retain lubricant within the polymeric coating 232, reducing friction between the rotating drive shaft 220 and the catheter 216. For example, where the catheter 216 must curve to conform to the curving vasculature of the human body, the drive shaft 220 may be forced against the inner surface 224. Without the polymeric coating 232, this force may push lubricant out from between the outer surface 230 of the drive shaft 220 and the inner surface 224 of the catheter 216. With the polymeric coating 232, lubricant remains between the outer surface 230 and the inner surface 224, reducing friction between the rotating drive shaft 220 and the catheter 216, which may otherwise generate heat and particles which may result in a failure of the rotational atherectomy catheter 202.

In some embodiments, a protective coating, such as the protective coating 142 described above in reference to FIG. 4A or 4B may cover all or at least a portion of the polymeric coating 232. In some embodiments, the protective coating 142 may have a higher modulus of elasticity than the polymeric coating 232. That is, the polymeric coating 232 may be more flexible than the protective coating 142. Additionally or alternatively, the protective coating 142 may be more resistive to wear from contact with the inner surface 224 as compared to the polymeric coating 232.

The medical device 200 may be formed as described above for the medical device 100 in reference to FIG. 5. The medical device 200 generically represents, but is not limited to, systems such as chronic total occlusion devices, ultrasonic coronary imaging catheter, or atherectomy catheters used with or without a guide wire.

In some embodiments, once the microstructures are formed, a spiral path through the microstructures may be formed along the wire by removing the microstructures and a portion of the underlying bulk material along the spiral path around the wire. The spiral path may function as an Archimedes screw to drive lubricant forward as it rotates, distributing the lubricant along the wire. The pitch angle of the spiral path may be between about 20 degrees and 70 degrees. The spiral path may be formed by treating the surface with laser irradiation at fluence levels just above the ablation threshold for the polymer coating.

Embodiments also include other medical devices including a tubular body having a lumen and a wire extending through the lumen, such as an endoscope. A polymeric coating including a plurality of microstructures disposed on the wire, as described above, may ease the movement of the wire through the endoscope, especially when the endoscope has traversed through various curves in the intestines. In some embodiments, in which a spiral path is formed on the wire as described above, as the wire is slowly turned, the microstructures could sweep lubricant around the wire and forward along the length of the wire, while reducing friction between the lumen and the wire.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical device comprising:
a catheter having a distal end and a proximal end;
a lumen extending through the catheter from the distal end to the proximal end;
a drive shaft extending through the lumen from the distal end to the proximal end, wherein the drive shaft is a helically coiled wire having an outer surface; and
a polymeric coating on at least a portion of the outer surface of the drive shaft, wherein the coating comprises a bulk material and a plurality of flexible polymeric microstructures disposed on the bulk material, wherein the flexible polymeric microstructures extend outwardly from a surface of the polymeric coating.

2. The medical device of claim 1, wherein the flexible polymeric microstructures include a first end and a second end, and the distance from the first end to the second end is from 5 micrometers to 100 micrometers.

3. The medical device of claim 1, wherein the flexible polymeric microstructures are integral with the polymeric coating.

4. The medical device of claim 1, wherein the coating includes at least one member selected from the group consisting of ethylene tetrafluoroethylene (ETFE) and polyethylene terephthalate (PET).

5. The medical device of claim 1, and further comprising a protective coating on at least a portion of the flexible polymeric microstructures.

6. The medical device of claim 5, wherein the protective coating has a thickness of 3 nanometers to 30 nanometers.

7. The medical device of claim 5, wherein the protective coating has a higher modulus of elasticity than the polymeric coating.

8. The medical device of claim 1, and further comprising a lubricant between at least a portion of an inner surface of the catheter and at least a portion of the flexible polymeric microstructures.

9. A medical device comprising:
a tubular body having a distal end and a proximal end and including at least one lumen and at least one inner surface extending from the distal end to the proximal end;
a wire extending through the at least one lumen and having an outer surface; and
a polymeric coating disposed on at least a portion of the outer surface of the wire, wherein the polymeric coating comprises a bulk material and a plurality of flexible polymeric microstructures disposed on the bulk material, wherein the flexible polymeric microstructures extend outwardly from a surface of the polymeric coating and have at least one point of contact with the inner surface of the tubular body.

10. The medical device of claim 9, wherein the flexible polymeric microstructures are integral with the polymeric coating.

11. The medical device of claim 9, wherein the flexible polymeric microstructures can bend at least 0.0015 radians.

12. The medical device of claim 9, wherein the flexible polymeric microstructures have a minimum diameter and a length that is at least twice the minimum diameter.

13. The medical device of claim 9, and further comprising a protective coating on at least a portion of the flexible polymeric microstructures.

14. The medical device of claim 13, wherein the protective coating has a higher modulus of elasticity than the polymeric coating.

15. The medical device of claim 9, wherein the tubular body is a catheter and the wire is a drive shaft.

16. A method of forming a medical device, the method comprising:
forming a polymeric coating on an outer surface of a wire;
exposing the polymeric coating to laser energy at a fluence level below the ablation threshold to form a plurality of flexible polymeric microstructures extending outward from a surface of the coating; and
positioning the wire within a lumen of a tubular body.

17. The method of claim 16, wherein the laser energy is a polarized pulsed laser irradiation.

18. The method of claim 16, and further comprising applying a protective coating on at least a portion of the flexible polymeric microstructures.

19. The method of claim 16, and further comprising dispensing a lubricant between the flexible polymeric microstructures and the tubular body.

20. The method of claim 16, wherein the tubular body is a catheter and the wire is a drive shaft.

* * * * *